United States Patent [19]

Leonard

[11] Patent Number: 4,478,578
[45] Date of Patent: Oct. 23, 1984

[54] HANDLE FOR DENTAL CANAL ROTARY INSTRUMENT AND METHOD OF MANUFACTURING SAME

[75] Inventor: Henri Leonard, Besancon, France
[73] Assignee: Micro-Mega S.A., Besancon, France
[21] Appl. No.: 344,834
[22] Filed: Feb. 1, 1982

[30] Foreign Application Priority Data

Feb. 12, 1981 [FR] France .................. 81 02755

[51] Int. Cl.³ .............................................. A61C 3/02
[52] U.S. Cl. ............................... 433/165; 408/226
[58] Field of Search ................ 433/165, 166, 102, 141;
408/226; 145/61 C, 6 R

[56] References Cited

U.S. PATENT DOCUMENTS

| 1,499,346 | 7/1924 | Chott | 433/166 |
| 1,512,920 | 10/1924 | Galvin | 145/61 C |
| 2,606,366 | 8/1952 | Stevens | 433/166 |
| 4,135,847 | 1/1979 | Hemmings | 408/226 |

FOREIGN PATENT DOCUMENTS

| 7601126 | 2/1976 | Netherlands | 408/226 |
| 321980 | 5/1957 | Switzerland | 408/226 |

Primary Examiner—John J. Wilson
Attorney, Agent, or Firm—Jordan and Hamburg

[57] ABSTRACT

This dental canal rotary instrument comprises a handle having a hollow metal sleeve surrounding concentrically the inoperative end of the instrument shank; a suitable plastic material is cast into a mold so as to fill the gap left between the sleeve and the shank to form a plastic core embedding the shank, the latter protruding from at least one of the sleeve ends; a notch is formed in the sleeve for anchoring the sleeve and the plastic core, and a flat face is provided on the embedded shank end, in order to improve the adherence of the sleeve, core and shank to one another.

5 Claims, 10 Drawing Figures

Fig. 1
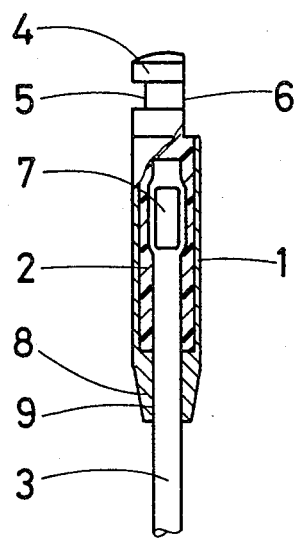
Fig. 2
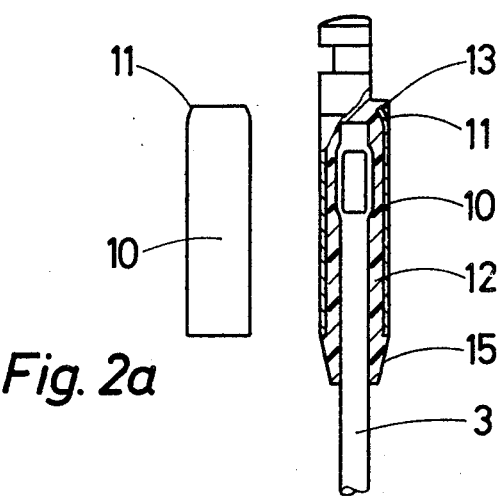
Fig. 2a
Fig. 3
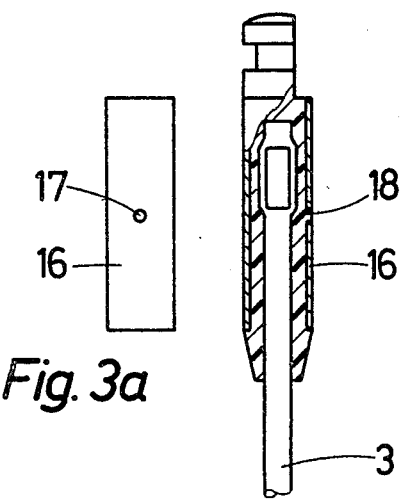
Fig. 3a
Fig. 4
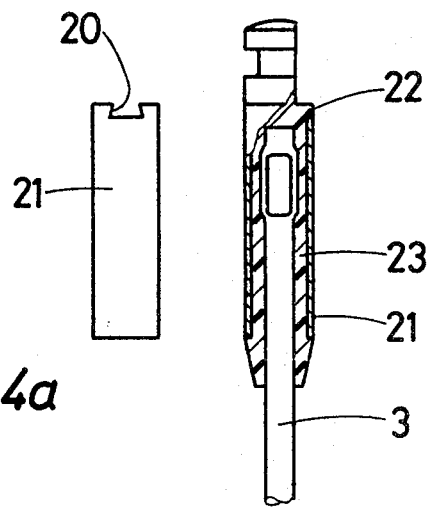
Fig. 4a

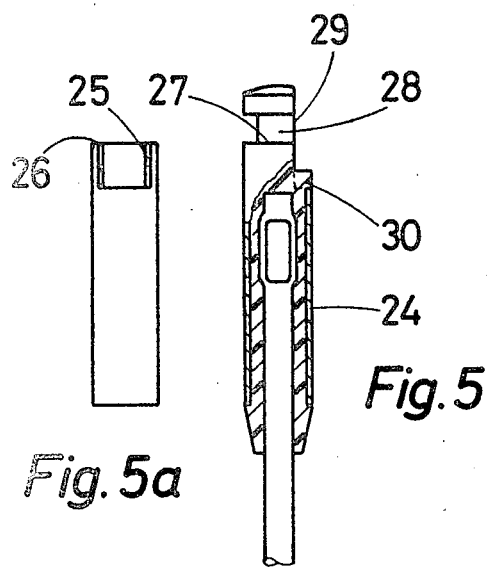
*Fig. 5a*  *Fig. 5*
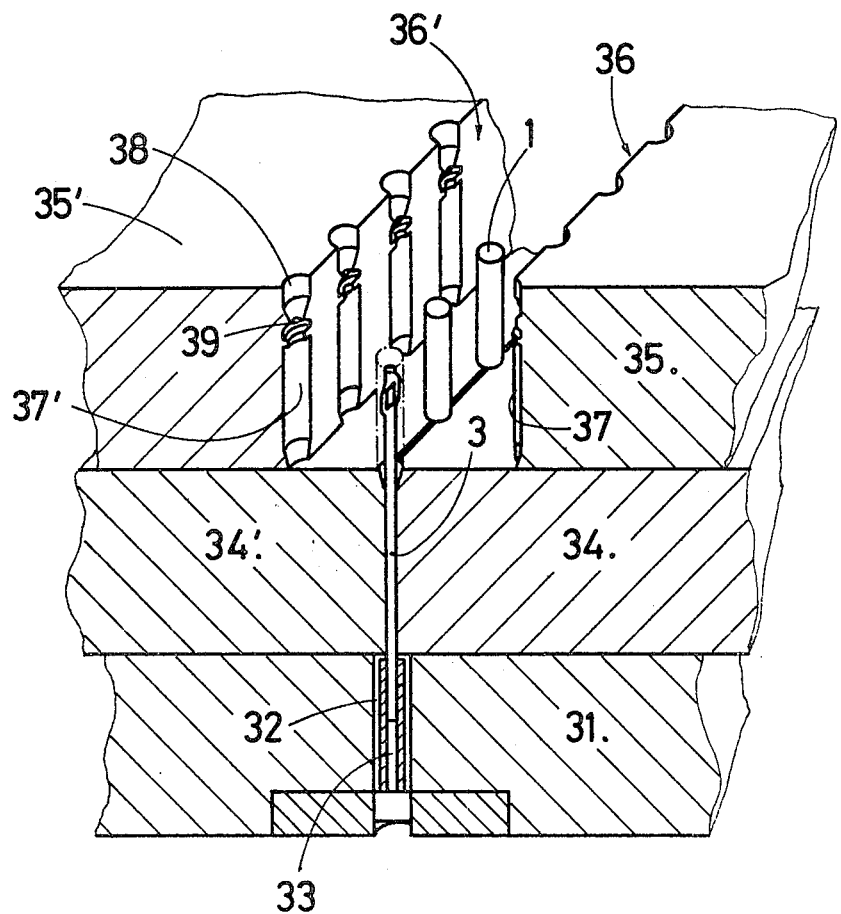
*Fig. 6*

HANDLE FOR DENTAL CANAL ROTARY INSTRUMENT AND METHOD OF MANUFACTURING SAME

BACKGROUND OF THE INVENTION

This invention relates to a dental canal rotary instrument comprising a handle. This instrument can be a reamer, a drill, a bur, a broach, a spiral filler or the like, and being operated according to its specific nature with a contra-angle driven for continuous or alternating rotation. The purpose of the handle is to hold the instrument in the contra-angle and to rotatably drive the instrument.

THE PRIOR ART

Up to now, the handles of such dental canal instruments consisted of metal or plastics, and the rear end of the instrument shank is rigidly fixed, for example by sticking, in the metal handle, or embedded by molding in the plastic material. Such dental canal instruments are manufactured with different lengths and diameters, and to facilitate their ready identification different colors are used; thus, in the case of metal handles, notably of aluminium, the aluminium is colored, and in the case of plastic handles, the whole body is color-impregnated. However, this method may constitute an inconvenience notably when cleaning or disinfecting the instrument. In fact, since the instruments must be disinfected after each use, that is, very frequently, they are prone to undergo some damage; thus, notably, aluminium handles are corroded by the caustic soda constituting the stock disinfectant, and plastic handles tend to swell when formol is used as a disinfectant.

SUMMARY OF THE INVENTION

It is the chief object of the present invention to avoid the inconveniences set forth hereinabove by providing a handle for a rotary dental canal instrument, characterized in that it consists of a cylindrical metal sleeve adapted to receive the inoperative end of the instrument shank, the gap left between the sleeve and the shank being filled with cast plastic material constituting a core adapted to fix the shank in the sleeve, said core projecting from the sleeve end to constitute the head of the instrument, at least one anchoring point being provided between the sleeve and the plastic core.

Thus, a compound handle, less fragile than a handle consisting only of plastic material, is obtained, the sleeve portion of this handle consisting preferably of German silver or nickel-plated brass, and having a good resistance to chemicals such as soda or formol.

This invention also relates to a method of manufacturing a handle of the type broadly set forth hereinabove, this method comprising the steps of disposing the shank of the instrument into a mold having an impression corresponding to the final shape of the desired handle, the shank being properly positioned and held both longitudinally and axially; slipping on the end of said shank a hollow metal sleeve also properly positioned and held longitudinally, the length of said sleeve being shorter than that of said mold and the outer sleeve diameter of said sleeve corresponding to the diameter of the mold impression, whereafter the mold is closed and a suitable molten plastic material is cast into it to fill up all the hollow portions of the sleeve and mold and embed the shank in a core of plastic material.

The attached drawings illustrate diagrammatically by way of example various forms of embodiment of the handle for dental canal rotary instruments according to the present invention.

THE DRAWINGS

FIG. 1 is a part-sectional and elevational view of a typical handle in which the instrument shank is inserted;

FIGS. 2 to 5 are similar views of four other forms of embodiment;

FIGS. 2a to 5b are side elevational views of the sleeves corresponding to the four forms of embodiment of FIGS. 2 to 5; and FIG. 6 is a diagrammatic perspective view of a mold suitable for carrying out the method of this invention.

DESCRIPTION OF THE PREFERRED EMBODIMENT

Referring to FIG. 1 of the drawings, illustrating a first form of embodiment of the handle according to the invention, it will be seen that this handle comprises a cylindrical hollow metal sleeve 1, for example of German nickel or nickel-plated brass, in which a plastic core 2 is molded. Firstly, the tool shank 3 is positioned in the sleeve 1 prior to the molding operation so that its central axis merges with the sleeve axis, so that the shank is safely and firmly embedded in the plastic core 2 and therefore adheres to both the core and the sleeve.

The form of the mold impression is such that the molded plastic projects somewhat from the upper end of the sleeve, as shown in the drawings, to form a head 4 provided preferably with a circular groove 5 and a flat lateral face 6 for both coupling and rotatably driving the sleeve in the contra-angle.

The rear end of shank 3 embedded in the plastic core 2 comprises preferably a lateral flat face 7 affording a better axial and rotational coupling between the shank and the plastic core.

In the form of embodiment illustrated, the lower portion of the sleeve 1 is tapered and has an axial bore 9 formed therein; the diameter of this bore 9 corresponds to the diameter of the shank 3.

A plurality of handles of this type may be molded in a common mold, for example the mold illustrated in FIG. 6, which comprises a base plate 31 in which a plurality of orifices 32 are formed, each orifice containing a stop member 33 for positioning the end of the shank of the root canal rotary instrument 3 in the longitudinal direction. Mounted on this support are a first pair of jaws 34,34' adapted to be moved firstly away from each other for positioning the shanks of the instruments 3 and subsequently towards each other for clamping and holding said shanks in position while constituting the lower or bottom wall of the mold proper.

Another pair of jaws 35,35' having formed in their registering faces 36,36' the hollow half-impressions 37,37' of the handle are firstly moved away from each other when fitting in position the instrument shanks 3, and then pressed against each other before casting the molten plastic material. However, before closing the mold, the sleeves 1 are slipped on the ends of shanks 3 and positioned automatically and accurately in relation thereto when the second pair of jaws 35,35' is closed. In this closed mold condition the plastic material is cast at a temperature of about 230° C. into the feed holes 38 leading through a neck portion 39 into the mold cavities 37,37'. The molten plastic is filled in the hollow portions of the sleeve 1 and mold 37,37', thus embedding the shank ends. When the plastic material has cooled down sufficiently the mold is opened and the casting plugs 38 thus obtained are severed at their neck portion 39 constituting incipient breaking points from the molded handles.

The plastic section 4 protruding from the end of sleeve 1 to constitute the above-mentioned head may advantageously be used for identifying the instrument number by utilizing plastic products of different colors. Besides, this multi-colored portion remains visible when the instruments are stored in a sterilization box.

The diameter of the plastic handle section which protrudes from the sleeve end may be smaller than the sleeve diameter to compensate any possible swelling of this section as a consequence of the residence time of the instrument in a formol bath, without interfering with the introduction and positioning of the instrument in the contra-angle.

FIGS. 2 and 2a illustrate a second form of embodiment of the handle. In this case, the sleeve 10 has a slightly tapered end 11 over which a plastic rim is formed during the molding operation, thus providing a convenient means for positively anchoring the sleeve and the plastic filling to each other. As in the preceding form of embodiment, the instrument shank 3 is embedded in the plastic core 12 but in this modified version the core 12 comprises on the shank side a tapered extension 15 constituting the lower portion of the handle.

In FIGS. 3 and 3a a third form of embodiment of the handle and/or sleeve is proposed, wherein the sleeve 16 has formed through its wall a radial hole 17 which, during the molding step, is filled with plastic 18 in order to afford a more reliable anchoring of the two component elements to each other.

In the fourth form of embodiment illustrated in FIG. 4, and FIG. 4a, a dovetail notch 20 is formed in the upper edge of the sleeve 21 for mutually coupling the core 23 and sleeve 21 by means of a plastic projection 22 engaging said notch 20 when molding the core 23.

FIGS. 5 and 5a illustrate a fifth form of embodiment of the handle in which the metal sleeve 24 comprises at its upper end a rectangular notch 25; furthermore, the edge 26 of this sleeve 24 is adapted to coincide with the lower edge 27 of the circular groove 28 formed in the head. The dimensions of this notch 25 are so calculated that the flat face 29 of the head is flush with the edges of said notch, and that only a small projection 30 of the plastic core engages the bottom of said notch for mutually anchoring the core and sleeve. This arrangement strengthens the sleeve portion likely to be weakened by the presence of the circular groove 28.

Other means could of course be used for preventing and undesired uncoupling between the two materials; thus, notably, female screw-threads or any other suitable retaining means could be provided on the inner wall of the sleeve, without departing from the scope of the invention.

What is claimed is:

1. A dental canal rotary instrument comprising:
   an instrument shank having an inoperative rear end,
   a cylindrical metal sleeve having at least one hole therein, said inoperative end of the shank being situated in the metal sleeve so that a gap is formed between the metal sleeve and the shank, and
   a plastic material filling the hole in the sleeve and the gap between the metal sleeve and the shank so that the shank is immovably held inside the metal sleeve, said plastic material forming a head extending upwardly beyond the metal sleeve and the inoperative rear end of the shank, said head having a flat lateral face extending along the longitudinal direction thereof and an arcuate groove extending perpendicular to and up to the edges of the flat lateral face, said plastic material further forming a frustoconical section extending downwardly from the sleeve to the shank.

2. A dental canal rotary instrument comprising:
   an instrument shank having an inoperative rear end,
   a cylindrical metal sleeve having at least one notch formed in one end thereof, said inoperative end of the shank being situated in the metal sleeve so that a gap is formed between the metal sleeve and the shank, and
   a plastic material filling the notch of the sleeve and the gap between the metal sleeve and the shank so that the shank is immovably held inside the metal sleeve, said plastic material forming a head extending upwardly beyond the metal sleeve and the inoperative rear end of the shank, said head having a flat lateral face extending along the longitudinal direction thereof and an arcuate groove extending perpendicular to and up to the edges of the flat lateral face, said plastic material further forming a frustoconical section extending downwardly from the sleeve to the shank.

3. A dental canal according to claim 2, in which said notch of the sleeve is of a dovetail configuration so that the sleeve does not accidentally move relative to the plastic material in the longitudinal direction.

4. A dental canal according to claim 2, in which said flat lateral face of the head is flush with longitudinal edges of the notch of the sleeve, and an upper lateral edge of the sleeve is flush with a lower edge of the circular groove.

5. A dental canal rotary instrument comprising:
   an instrument shank having an inoperative rear end,
   a cylindrical metal sleeve having internal screw threads formed on an inner wall thereof, said inoperative rear end of the shank being situated in the metal sleeve so that a gap is formed between the metal sleeve and the shank, and
   a plastic material filling the gap between the metal sleeve and the shank so that the shank is immovably held inside the sleeve, said plastic material forming a head extending upwardly beyond the metal sleeve and the inoperative rear end of the shank, said head having a flat lateral face extending along the longitudinal direction thereof and a circular groove extending perpendicular to and up to the edges of the flat lateral face, said plastic material further forming a frustoconical section extending downwardly from the sleeve to the shank.

* * * * *